United States Patent
Bell et al.

(10) Patent No.: US 9,807,999 B2
(45) Date of Patent: Nov. 7, 2017

(54) FORMULATIONS

(75) Inventors: Gordon Alastair Bell, Bracknell (GB); Anne Waller, Bracknell (GB); Jeffrey Steven Wailes, Bracknell (GB)

(73) Assignee: Syngenta Limited, Guildford (GB)

( * ) Notice: Subject to any disclaimer, the term of this patent is extended or adjusted under 35 U.S.C. 154(b) by 425 days.

(21) Appl. No.: 13/812,223

(22) PCT Filed: Jul. 26, 2011

(86) PCT No.: PCT/IB2011/053325
§ 371 (c)(1),
(2), (4) Date: Apr. 8, 2013

(87) PCT Pub. No.: WO2012/014152
PCT Pub. Date: Feb. 2, 2012

(65) Prior Publication Data
US 2016/0000067 A1 Jan. 7, 2016

(30) Foreign Application Priority Data
Jul. 27, 2010 (GB) .................................. 1012586.2

(51) Int. Cl.
| | |
|---|---|
| *A01N 25/02* | (2006.01) |
| *A01N 25/04* | (2006.01) |
| *A01N 43/54* | (2006.01) |
| *A01N 43/56* | (2006.01) |
| *A01N 43/653* | (2006.01) |
| *C07C 69/78* | (2006.01) |
| *A01N 37/34* | (2006.01) |

(52) U.S. Cl.
CPC ............. *A01N 25/04* (2013.01); *A01N 25/02* (2013.01); *A01N 43/54* (2013.01); *A01N 43/56* (2013.01); *A01N 43/653* (2013.01); *C07C 69/78* (2013.01)

(58) Field of Classification Search
CPC ........ C07C 69/78; A01N 25/02; A01N 43/54; A01N 43/56; A01N 43/653; A01N 43/40; A01N 37/34; A01N 25/04
See application file for complete search history.

(56) References Cited

U.S. PATENT DOCUMENTS

2004/0063834 A1    4/2004   Duran Gonzalez

FOREIGN PATENT DOCUMENTS

| EP | 0268927 | | 6/1988 | |
|---|---|---|---|---|
| IL | 0058111 A | * | 4/1984 | |
| WO | 97/16481 | | 5/1997 | |
| WO | WO 2004035589 A1 | * | 4/2004 | ............. A01N 43/32 |

OTHER PUBLICATIONS

Santaniello, E. et. al., Journal of Molecular Catalysis B: Enzymatic, 2006, Elsevier, vol. 40, pp. 81-85.*
Hecker et. al., CAS STN Abstract, publ. 1971.*
International Search Report, International Application No. PCT/IB2011/053325, completion date: Jan. 11, 2011.
E P Kundig: Chem. Comm., Jan. 1, 2008, pp. 3519-3521.
Garti, Nissim et al: "Emulsions of Essential Oils for Citrus Beverages", Database accession No. 1985:61071, Apr. 30, 1984.
Keil, Karl H. et al: "Modified aminoplast", Database accession No. 1976:434772, Apr. 1, 1976.
Amato, Steven W. et al: "Polymer films containing butylphthalimide isopropylphthalimide for nailpolishes", Database accession No. 2002:977616, Dec. 27, 2002.
Fujioka, Hiromichi et al: "Reaction of diols and triols with trialkyl orthoesters: facile one-pot formation of oxacyclic compounds from triols", Database accession No. 1994:134197, 1993.
Vedrenne, Emeline et al: "Homologation of Boronic Esters with Lithiated Epoxides for the Stereocontrolled Synthesis of 1.2- and 1,3-Diols and 1,2,4-Triols", Database accession No. 2008:1475468, 2009.
Zecha, Helmut et al: "Formaldehyde-free emulsion polymer dispersion composition including polyvinyl alcohol as colloidal stabilizer providing improved heat resistance", Database accession No. 2008:1472497, Dec. 10, 2008.
Ikejiri M et al: "A novel and efficient method for inside selective esterification of terminal vic-diols", Tetrahedron Letters, Elsevier, Amsterdam, NL, vol. 45, No. 6, Feb. 2, 2004, pp. 1243-1246.
Marcel G. R. Ter Veld et al: "Estrogenic Potency of Food-Packaging-Associated Plasticizers and Antioxidants as Detected in ER[alpha] and ER[beta] Reporter Gene Cell Lines", Journal of Agricultural and Food Chemistry, vol. 54, No. 12, Jun. 1, 2006.
McCloskey, Chester M. et al: "Nonhazardous ketone peroxide compositions as polymerization initiators", Database accession No. 1972:420411, Mar. 14, 1972.

* cited by examiner

*Primary Examiner* — Sarah Pihonak
(74) *Attorney, Agent, or Firm* — James Cueva

(57) ABSTRACT

This invention relates to a formulation comprising a compound of formula (I) where R1 is hydrogen, methyl, ethyl, propyl or butyl; R2 is methyl or ethyl; R3 is hydrogen, methyl or ethyl; and n is 1, 2 or 3; to the use of a compound of formula (I) as a solvent; and to certain novel compounds of formula (I).

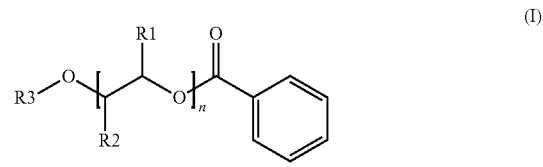

(I)

4 Claims, No Drawings

FORMULATIONS

This application is a 371 of International Application No. PCT/IB2011/053325 filed Jul. 26, 2011, which claims priority to GB 1012586.2 filed Jul. 27, 2010 the contents of which are incorporated herein by reference.

This invention relates to the use of certain alkylene glycol benzoate compounds as solvents, especially in formulations, particularly in agrochemical formulations and in environmentally friendly formulations; and to certain novel compounds. The solvents of the present invention are found to be particularly effective when solubilising pesticides of the families strobilurins, triazoles and succinate dehydrogenase inhibitors (SDHI) (particularly pyrazoles; suitably pyrazam chemistry).

Nowadays, the Formulation Chemist is required to address a number of environmental criteria when developing new formulations. Ideally, a suitable solvent will display many or all of the following properties: an excellent dissolving power for pesticides or other organic molecules; made from plant or animal renewable resources; low skin irritation; low ecotoxicity, for example to daphnia; low volatile organic content; and a high flash point. The compounds of the present invention each display all or many of these properties, in particular an excellent dissolving power; the compounds may be used effectively as solvents.

Accordingly, the present invention provides a formulation comprising a compound of formula (I)

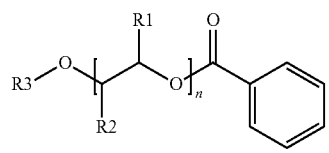

(I)

where $R^1$ is hydrogen, methyl, ethyl, propyl or butyl; $R^2$ is methyl or ethyl; $R^3$ is hydrogen, methyl or ethyl; and n is 1, 2 or 3.

Propyl and butyl groups are straight or branched chains. Examples are iso-propyl, n-propyl, n-butyl, sec-butyl and tert-butyl.

Suitably $R^1$ is H.
Suitably $R^2$ is methyl.
Suitably $R^3$ is H.
Suitably n is 1.
Suitably the invention provides the use of a compound of formula (I) in an agrochemical formulation.

The compounds of the present invention may be used as solvents.

Many of the compounds disclosed by the present invention are novel.

Therefore in a further aspect, the present invention provides a compound of formula (I) as defined above; provided that the compound is not 2-hydroxypropyl benzoate, 2-hydroxy-1-methylethyl benzoate, 1,2 butanediol-2-benzoate, 1,2 butanediol-1-benzoate or 1-propanol-2(2-hydroxypropoxy)-1-benzoate.

Table 1 provides structures and certain spectroscopic data for suitable compounds of formula (I):

TABLE 1

| Compound Number | $R^1$ | $R^2$ | $R^3$ | n | $MH^+$ from GCMS | IR band $cm^{-1}$ OH | IR band $cm^{-1}$ ester | IR band $cm^{-1}$ aromatic |
|---|---|---|---|---|---|---|---|---|
| 1 | H | $CH_3$ | H | 1 | 181 | 3340 | 1712 | 1600 |
| 2 | H | $CH_2CH_3$ | H | 1 | 195 | 3355 | 1715 | 1600 |

The compounds of the present invention are easy to prepare; for instance, a glycol ether is reacted with an aromatic compound with a suitable leaving group, for example benzoyl chloride.

The compounds of the invention may be used in a variety of end use applications (including agrochemical formulations), particularly as solvents. These solvents may be used with a wide variety of materials, including herbicides, fungicides, acaricides, nematicides and insecticides [and also plant growth regulators].

The present invention encompasses all isomers, or mixtures of isomers, of compounds of formula (I) and also encompasses mixtures of two or more different compounds of formula (I).

The compounds of the invention may be used to formulate solutions of a variety of materials, including agrochemicals, which may be formulated as emulsion or dispersion concentrates, emulsions in water or oil, microencapsulated formulations, aerosol sprays or fogging formulations; and these may be further formulated into granular materials or powders, for example for dry application or as water-dispersible formulations. The solutions so formed may also be used directly on soil or plants or in other non-agrochemical applications.

Examples of such applications include paper making, water treatment, forestry applications, public health treatments, use in municipal pools and other water courses, in applications near rivers, lakes, reservoirs or seas and in applications where release to the atmosphere has to be minimised or controlled and where damage to the atmosphere is not desirable. Examples include use in exterior and interior paints, coatings, varnishes, waxes or other protectant layers or opacifiers, colourants or screens; in dyeing, pigmentation or the use of inks; in cleaning products designed for the home, garden or industrial applications; and in soap or detergent applications for industrial, home or environmental usage. The compounds of the present invention may also be used in shampoos, household detergency and in household cleaners [for example oven cleaners and surface cleaners].

The compounds of the present invention have exceptional dissolving power for a wide variety of agrochemicals, pharmaceuticals and other commercially valuable compounds, plus the dissolving power also extends to dissolution of dirt, grease or waxes.

The invention is illustrated by the following Examples in which:
g=grammes ° C.=degrees centigrade
Unless otherwise stated, each concentration is expressed as percentage by weight.

The solvents of the present invention are particularly effective when solubilising pesticides belonging to the families: strobilurins, triazoles and succinate dehydrogenase inhibitors (SDHI) (particularly pyrazoles; suitably pyrazam chemistry). This fact is demonstrated in the examples where it is shown that the solubility of the pesticides azoxystrobin, difenoconazole and isopyrazam are higher in the solvent propylene glycol benzoate than in a series of commonly used solvents. Surprisingly the solubility of cyprodinil, chlorothalonil and bicyclopyrone in propylene glycol benzoate is lower than in the same series of common solvents. Solubilities are quoted as percentage w/w at 20° C.

EXAMPLE 1

This Example illustrates the high solubility of each of a number of agrochemical active ingredients in solvents of the present invention [compounds 1 and 2 of Table 1].

A glass vial was approximately one eighth filled with an active ingredient [AI] and then solvent [in this example, propylene glycol benzoate or butylene glycol benzoate] was added until the vial was approximately one third full. The resultant sample was mixed with a Whirlimixer™ and was then stored at 25° C. The sample was checked every few days; if there was no solid active ingredient present then additional active ingredient was added; if there was no liquid remaining then additional solvent was added. This procedure was repeated until the sample had equilibrated for 4 weeks following the final addition of either active ingredient or solvent. The supernatant liquid layer was then analysed by gas chromatography for active ingredient concentration; the results are given in Table 2:

TABLE 2

| Active Ingredient | Solubility in propylene glycol benzoate at 25° C. (% w/w) | Solubility in butylene glycol benzoate at 25° C. (% w/w) |
|---|---|---|
| Difenoconazole | 50.5 | — |
| Chlorothalonil | 1.32 | — |
| Cyprodinil | 18.4 | — |
| 4-Hydroxy-3-[2-(2-methoxyethoxymethyl)-6-trifluoromethylpyridine-3-carbonyl]-bicyclo[3.2.1]oct-3-en-2-one | 27.4 | — |
| Azoxystrobin | 5.5 | 8.1 |
| Cyproconazole | 4.5 | 6.9 |
| Isopyrazam | 12.7 | 12.4 |

EXAMPLE 2

This Example shows that the solvents of the present invention are particularly effective when solubilising pesticides belonging to the families: strobilurins, triazoles and succinate dehydrogenase inhibitors (SDHI) (particularly pyrazoles; suitably pyrazam chemistry). Tables 3a and 3b show the solubility of the pesticides azoxystrobin, difenoconazole, isopyrazam, cyprodinil, chlorothalonil and bicyclopyrone in the solvent propyle glycol benzoate [compound 1 of Table 1]. For comparison the solubilities in a series of commonly used solvents are also tabulated. The data show that in most cases the propylene glycol benzoate is a better solvent for the first three pesticides (respectively a triazole, an SDHI and a strobilurin,) than are the other common solvents. Solubilities are quoted as percentage w/w at 20° C.

TABLE 3a

| Solvent | Difenoconazole | Isopyrazam | Azoxystrobin |
|---|---|---|---|
| Propylene glycol benzoate | 50.5 | 12.7 | 5.5 |
| n-Butylbenzoate | 29.4 | 7.6 | 4.0 |
| Solvesso ™ 100 ND/ULN | 37.8 | 0.0 | 1.7 |
| Solvesso ™ 200 ND/ULN | 37.7 | 5.8 | 5.6 |
| Dowanol ™ PnB | 34.4 | 8.8 | 1.3 |
| Isobornyl acetate | 24.9 | 6.8 | 1.6 |
| Benzoflex ™ 9-88 | 19.8 | 6.3 | 4.2 |
| Butyl lactate | 47.1 | 16.5 | 4.6 |
| Dowanol ™ PGDA | 34.1 | 6.9 | 9.4 |
| Benzyl acetone | 44.9 | 12.6 | 14.1 |
| Benzyl acetate | 46.0 | 8.9 | 13.8 |
| Triacetin | 22.3 | 4.3 | 6.4 |

TABLE 3b

| Solvent | Cyprodinil | Bicyclopyrone | Chlorothalonil |
|---|---|---|---|
| Propylene glycol benzoate | 18.4 | 27.4 | 1.3 |
| n-Butylbenzoate | 35.5 | 45.6 | 2.3 |
| Solvesso ™ 100 ND/ULN | 31.1 | 52.3 | 7.1 |
| Solvesso ™ 200 ND/ULN | 34.4 | 50.7 | 9.6 |
| Dowanol ™ PnB | 41.7 | 32.0 | 0.2 |
| Isobornyl acetate | 32.8 | 38.4 | 0.5 |
| Benzoflex ™ 9-88 | 22.6 | 23.2 | 1.9 |
| Butyl lactate | 52.5 | 48.6 | 0.4 |
| Dowanol ™ PGDA | 31.3 | 38.3 | 0.6 |
| Benzyl acetone | 39.6 | 53.0 | 2.8 |
| Benzyl acetate | 36.8 | 55.5 | 2.0 |
| Triacetin | 18.9 | 33.3 | 0.4 |

The invention claimed is:

1. A formulation comprising an agrochemical and a compound of formula (I)

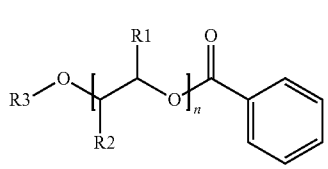

(I)

where $R^1$ is hydrogen, methyl, ethyl, propyl or butyl; $R^2$ is methyl or ethyl; $R^3$ is hydrogen, methyl or ethyl; n is 1 and wherein the agrochemical is azoxystrobin, difenoconazole or isopyrazam and the formulation is an emulsifiable concentrate or an emulsion.

2. A formulation as claimed in claim 1 where $R^1$ is hydrogen.

3. A formulation as claimed in claim 1 where $R^3$ is hydrogen.

4. A formulation as claimed in claim 2 where $R^3$ is hydrogen.

* * * * *